United States Patent
Harrison

(10) Patent No.: US 9,552,461 B2
(45) Date of Patent: Jan. 24, 2017

(54) FOOD PREPARATION SYSTEM AND METHOD

(76) Inventor: Chet Harrison, Corona del Mar, CA (US)

( * ) Notice: Subject to any disclaimer, the term of this patent is extended or adjusted under 35 U.S.C. 154(b) by 293 days.

(21) Appl. No.: 13/114,820

(22) Filed: May 24, 2011

(65) Prior Publication Data

US 2011/0289044 A1 Nov. 24, 2011

Related U.S. Application Data

(60) Provisional application No. 61/347,680, filed on May 24, 2010.

(51) Int. Cl.
*G06F 19/00* (2011.01)

(52) U.S. Cl.
CPC .................. *G06F 19/3475* (2013.01)

(58) Field of Classification Search
CPC .......... G06N 5/048; G06N 5/04; G06N 7/005; G06N 99/005; G06N 7/02; G06Q 10/10; G06F 9/44
USPC ........................ 706/52, 46, 45, 62
See application file for complete search history.

(56) References Cited

U.S. PATENT DOCUMENTS

| | | | |
|---|---|---|---|
| 5,960,440 A * | 9/1999 | Brenner et al. | |
| 6,789,067 B1 * | 9/2004 | Liebenow | 705/15 |
| 2001/0025279 A1 * | 9/2001 | Krulak et al. | 707/3 |
| 2002/0004749 A1 * | 1/2002 | Froseth et al. | 705/16 |
| 2003/0165799 A1 * | 9/2003 | Bisogno | 434/127 |
| 2003/0208383 A1 * | 11/2003 | Hauck et al. | 705/3 |
| 2005/0021361 A1 * | 1/2005 | Huang et al. | 705/1 |
| 2006/0020614 A1 * | 1/2006 | Kolawa et al. | 707/100 |
| 2006/0122468 A1 * | 6/2006 | Tavor | 600/300 |
| 2006/0195510 A1 * | 8/2006 | McNally | 709/203 |
| 2009/0083327 A1 * | 3/2009 | Ringham et al. | 707/104.1 |
| 2009/0125404 A1 * | 5/2009 | Mekonen et al. | 705/15 |
| 2009/0234712 A1 * | 9/2009 | Kolawa et al. | 705/10 |
| 2010/0115548 A1 * | 5/2010 | Leyvi | 725/34 |
| 2011/0218839 A1 * | 9/2011 | Shamaiengar | G06Q 30/0203 705/7.32 |

* cited by examiner

*Primary Examiner* — Stanley K Hill
*Assistant Examiner* — Ilya Traktovenko
(74) *Attorney, Agent, or Firm* — Rutan & Tucker LLP; Hani Z. Sayed

(57) ABSTRACT

A system and method for preparing food, involving a nutritional information module for aggregating nutritional and portion information of an entire menu to adjust serving weight by preferred caloric value. The system involves a scheduler module which compiles task information for any individual recipe. The scheduler module has a passive task time and/or an active task time and stamps the preparation time for a recipe. The system compiles and stores a cook's information for analyzing an individual cooking: style time. Moreover, the system involves a feedback module for predicting preparation time of any particular menu choice. Additionally, the system involves recipe data, an organizer, a shopping assistant, and a recommendation module to facilitate menu pairings as well as sourcing and purchasing, required ingredients, required cookware, and utensils for a recipe.

23 Claims, 3 Drawing Sheets

FOOD PREPARATION SYSTEM AND METHOD

CROSS-REFERENCE TO RELATED APPLICATIONS

This application claims the benefit of U.S. Provisional Patent Application No. 61/347,680, filed May 24, 2010 entitled "Food Preparation System and Method," which is incorporated herein by reference in its entirety.

FIELD OF THE INVENTION

The field of the invention is for the preparation of food. More specifically, the field of invention is for a system and method for scheduling and methodology for preparing a meal.

BACKGROUND

Preparing meals for a family can be very stressful, especially for individuals and families where both parents work full time. Preparing a meal for a family may often times lead to families going out to eat instead of preparing meals at home. The problem with eating outside the home, is that often times, the meals prepared at restaurants make use of processed foods that are neither healthy or calorie efficient. Nutritional information is often unknown and caloric intake is usually greatly increased over what would normally be prepared and consumed in the home.

When individuals do prepare meals in the home, often times the meals are pre-prepared from a package that is bought at a grocery store. While this type of food preparation can be easier and faster for the individual users, especially for families with little time to prepare food, the problems with these types of pre-prepared foods are that they are often similar to restaurant style food in that they are very much processed foods, with high caloric counts and with low nutritional value. Additionally, these pre-prepared foods can often be more expensive than the sum of their ingredients.

Another avenue that many individuals and families may prefer is to cook fresh meals utilizing fresh ingredients which allows for portion control, efficient use of nutritional value and proper caloric intake. While this type of cooking is more ideal and much more valuable, the downside to preparing fresh meals is that it requires fresh produce, whereby the individual user would need to purchase all the proper ingredients from a grocery store prior to preparing a meal for the family. Additionally, because all the ingredients need to be fresh, the preparation time is greatly increased because each ingredient may require prep work prior to introduction into the meal. Moreover, ingredients by themselves do not guarantee a good meal. Typically, the individual user will need some type of recipe to follow in order to prepare a good tasting meal. However, following a recipe or having all the correct ingredients for any particular recipe may be challenging for any specific individual. For example, many people are good at following recipes and following it quickly. However, for many individuals, it may take considerably more time to follow, learn and prepare a specific recipe. The dramatic difference in efficiency between the beginner and expert chef makes prep time predications extremely error prone. For example, although it should take an individual thirty minutes to prepare a particular recipe, some individuals may require much more time for the same recipe because of their particular cooking style or even distractions while they are cooking. So, what may look like an easy, quick cooking recipe may turn into a long and laborious process for some people.

Therefore, a need exists for a new and improved system and method to help individuals access cooking styles and preparation times. More specifically, what is needed is a new and improved system and method which allows individuals to view nutritional values associated with any particular menu or meal plan and utilize a user's recipe execution speed feedback in order to provide a personalized prediction of how long it will take to prepare any given menu. Moreover, a system and method is needed to organize recipe information including necessary ingredients and recommendations for accompanying dishes, drinks, desserts and the like.

SUMMARY OF THE INVENTION

The present invention provides a system and method for preparation of food. The system utilizes a nutritional information module which allows nutritional information to be aggregated for an entire menu along with portion information for any individual recipe. The system also utilizes a scheduler module which compiles task information for any individual recipe instruction. The schedule module may have a plurality of different task times per paragraph including a passive task time and/or an active task time with a task window for cooking time flexibility and may time stamp the time it takes to prepare any specific recipe. The schedule may compile cook information and store information in a memory bank for analysis of the individual cook's cooking style and cook time. Moreover, the system may also provide a feedback module which uses personal time co-efficients to predict how long it should take for any particular menu choice preparation. Additionally, the system may include any of the recipe data module, organizer module, shopping assistant modules and a recommendation module to help the individual cook and decide menu pairings for any particular recipe.

Among the many different possibilities contemplated, the system may allow for more efficient use of a food preparers time.

In an exemplary embodiment of the present invention, a food preparation system, the system comprising: a nutritional information module integrated into memory storage of a computing device; the computing device having at least a microprocessor and a storage drive; a scheduler module incorporated and stored in the storage device; and a feedback module.

In an exemplary embodiment, wherein said nutritional information module allows for adjustment of portions and caloric values based on ingredients input into the module.

In an exemplary embodiment, wherein said nutritional information module further aggregates the caloric and nutritional information for any particular menu choice.

In an exemplary embodiment, wherein said schedule module informs an individual of time needed to execute any specific paragraph of a recipe.

In an exemplary embodiment, wherein said schedule module has a passive task time module which provides additional time to complete any recipe task.

In an exemplary embodiment, wherein said feedback module includes a personal time co-efficient to predict the length of time to complete any specific paragraph of a recipe the user has never executed before.

In an exemplary embodiment, wherein any of a recipe data module, an organizer module, and a shopping assistant module.

In an exemplary embodiment, a recommendation module for recommending menu pairings, beverage pairings and dessert pairings for a particular recipe designated by an individual user.

In an exemplary embodiment of the present invention, a system for the preparation of food comprising: a processor; memory storing instructions that cause the processor to: aggregate nutritional information for an entire menu along with portion information; adjust serving weight by preferred caloric value for an individual recipe; compile task information for individual recipe items cook information; store information in a memory bank for analysis of an individual cook's cooking style and cook time; and predict a personal time co-efficients to predict how long it should take for any particular menu choice preparation.

In an exemplary embodiment, wherein the memory stores an instruction causing the processor to adjust portions and caloric values based on ingredients input into the system.

In an exemplary embodiment, wherein the memory stores an instruction causing the processor to aggregate the caloric and nutritional information for any particular menu choice.

In an exemplary embodiment, wherein the memory stores an instruction causing the processor to inform an individual of time needed to execute any specific paragraph of a recipe.

In an exemplary embodiment, wherein the memory stores an instruction causing the processor to provide additional time to complete any recipe task.

In an exemplary embodiment, wherein the memory stores an instruction causing the processor to predict the length of time to complete any specific paragraph of a recipe the user has never executed before.

In an exemplary embodiment, further comprising any of a recipe data module, an organizer module, and a shopping assistant module.

In an exemplary embodiment, wherein the memory stores an instruction causing the processor to recommend menu pairings, beverage pairings and dessert pairings for a particular recipe designated by an individual user.

In an exemplary embodiment, a method for the preparation of food comprising: aggregating nutritional information for an entire menu along with portion information; adjusting serving weight by preferred caloric value for an individual recipe; compiling task information for individual recipe items cook information; storing information in a memory bank for analysis of an individual cook's cooking style and cook time; and redirecting a personal time co-efficients to predict how long it should take for any particular menu choice preparation.

In an exemplary embodiment, providing a recipe data module, organizer module, shopping assistant modules and a recommendation module to help the individual cook decide of menu pairings for any particular recipe as well as source and purchase recipes, required ingredients, and required cookware and utensils.

In an exemplary embodiment, providing time stamping the time it takes to prepare any specific recipe.

In an exemplary embodiment, wherein the compiling task information for any individual recipe items step is based on each paragraph of the recipe.

In an exemplary embodiment, a system and method is provided for the preparation of food whereby the system includes a nutritional information module.

In yet another exemplary embodiment, a system and method is provided for the preparation of food whereby the system includes at least a scheduler module.

Still another exemplary embodiment is to provide a system and method for preparation of food whereby the system allows for delicious and healthy meals that are easy to prepare and guide the preparer through the cooking process.

In another exemplary embodiment, a system and method is provided for the preparation of food whereby the system allows the individual user to select and pair recipes and beverages when planning menus and meal plans.

Yet another exemplary embodiment is to provide a system and method for the preparation of food whereby the system allows the individual user to understand and adjust nutritional balances depending on the dietary restrictions or concerns of that individual user.

In yet another exemplary embodiment, a system and method for the preparation of food is provided whereby the system may allow the individual preparer to find and purchase the required ingredients, cookware, utensils and other tools required to prepare the desired food.

Still another exemplary embodiment is to provide a system and method for preparation of food whereby the system utilizes proprietary software stored in memory of a device such as a computer, hand-held, cellular phone, portable computing device and the like whereby the content may be downloaded to the device and utilized by the user where desired.

In another exemplary embodiment, a system and method is provided for the preparation of food whereby the system allows for the development of taste profiles depending on the feedback given to the system.

In an exemplary embodiment, a system and method is provided for the preparation of food whereby the system includes a feedback module which allows information to be input into the system by the individual preparer based on the preferences of that individual preparer.

Yet another exemplary embodiment is to provide a system and method for the preparation of food whereby the system includes a feedback module which provides feedback information to the preparer to access their preferences and timing to allow for preferred menus, preparation time, recipes and the like to be provided to the individual user.

Still another exemplary embodiment is to provide a system and method for preparation of food whereby the system allows the individual user to browse and purchase individual recipes from a remote server location.

In another exemplary embodiment, a system and method is provided for the preparation of food whereby the system may provide a user course, pairing or skill level to recommend specific menus or foods that will be easier or more difficult depending on information from that individual user.

Yet another exemplary embodiment is to provide a system and method for the preparation of food whereby the system may access remote location menus, recipes to provide menu pairings, along with beverage selections and other information to provide help to the individual food preparer depending on preferences and user inputted information.

Still another exemplary embodiment is to provide a system and method for preparation of food whereby the system utilizes a nutritional information module which may allow for alteration of servings so that the user will not have to adjust the necessary volumes while preparing a meal.

Still another exemplary embodiment is to provide a system and method for preparation of food whereby the system may utilize a schedule module whereby the user may create a menu and add recipes to create multiple course meals showing the critical path by blending and sorting each paragraph element of multiple recipes in the most efficient order.

Additionally, in an exemplary embodiment, a system and method for preparation of food is provided whereby the system may have a task window feature whereby the task window is bounded by the earliest time as task can be started, and produce an acceptable serving, and the start of the next dependent task. More flexible tasks can be rescheduled to earlier point in time. As servings scale the active time grows. If it overflows the task window a bottleneck is flagged. All or a portion of any task can be reassigned to another chef.

In another exemplary embodiment, it is contemplated that the system may be configured for the individual food preparers preferences.

In yet another exemplary embodiment, it is contemplated that the system and method may have a recipe data module.

A further exemplary embodiment contemplates that the system may have any of the organizer module, a shopping assistant module and the like.

In yet another exemplary embodiment, a system and method for the preparation of food is provided whereby the system may allow for recommendations to be made based on other users who pair the particular menu options.

In another exemplary embodiment, it is contemplated that the system may have a recommendation module which may combine menu options including different dishes, beverages, desserts and the like.

Further, a contemplated exemplary embodiment of the system is to allow the individual user to mix and match menu options as desired.

Additionally, in an exemplary embodiment, a system and method for the preparation of food is provided whereby the system provides at least a feedback module which uses personal time co-efficients to predict the length of time to prepare specific recipe and/or dish.

In yet another exemplary embodiment, it is contemplated that a system and method for the preparation of food may be provided whereby the system may schedule and inform the individual user when it is the appropriate time for any one cooking procedure.

Yet another exemplary embodiment of the present invention may be a system and method for the preparation of a food dish whereby the system allows for configuration of the system depending on individual user needs.

In an exemplary embodiment of the present invention, a system and method for the preparation of a food product is provided whereby the system may allow for download and viewing of appropriate task functions as desired by the individual user.

In yet another exemplary embodiment another generate a shopping list with ingredients called to the number of servings and serving size.

In yet another exemplary embodiment scale the final serving weight of any recipe by adjusting the number of desired calories per serving.

In yet another exemplary embodiment use the user's location to find venders of all the required ingredients in the shopping list.

In yet another exemplary embodiment find and appoint a default list of multiple ingredient vendors searching for each item in the vender's inventory in descending preferred order.

In yet another exemplary embodiment the system or method provides for purchasing the shopping list items from the application for one of three fulfillment methods: Mail order, pick up, or delivery.

In yet another exemplary embodiment, assign any vender as the default vender for any specific ingredient.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWING

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale. For clarity it is to be understood that the words "including," "has," and "having," as used herein, including the claims, shall have the same meaning as the word "comprising."

Figure 1:
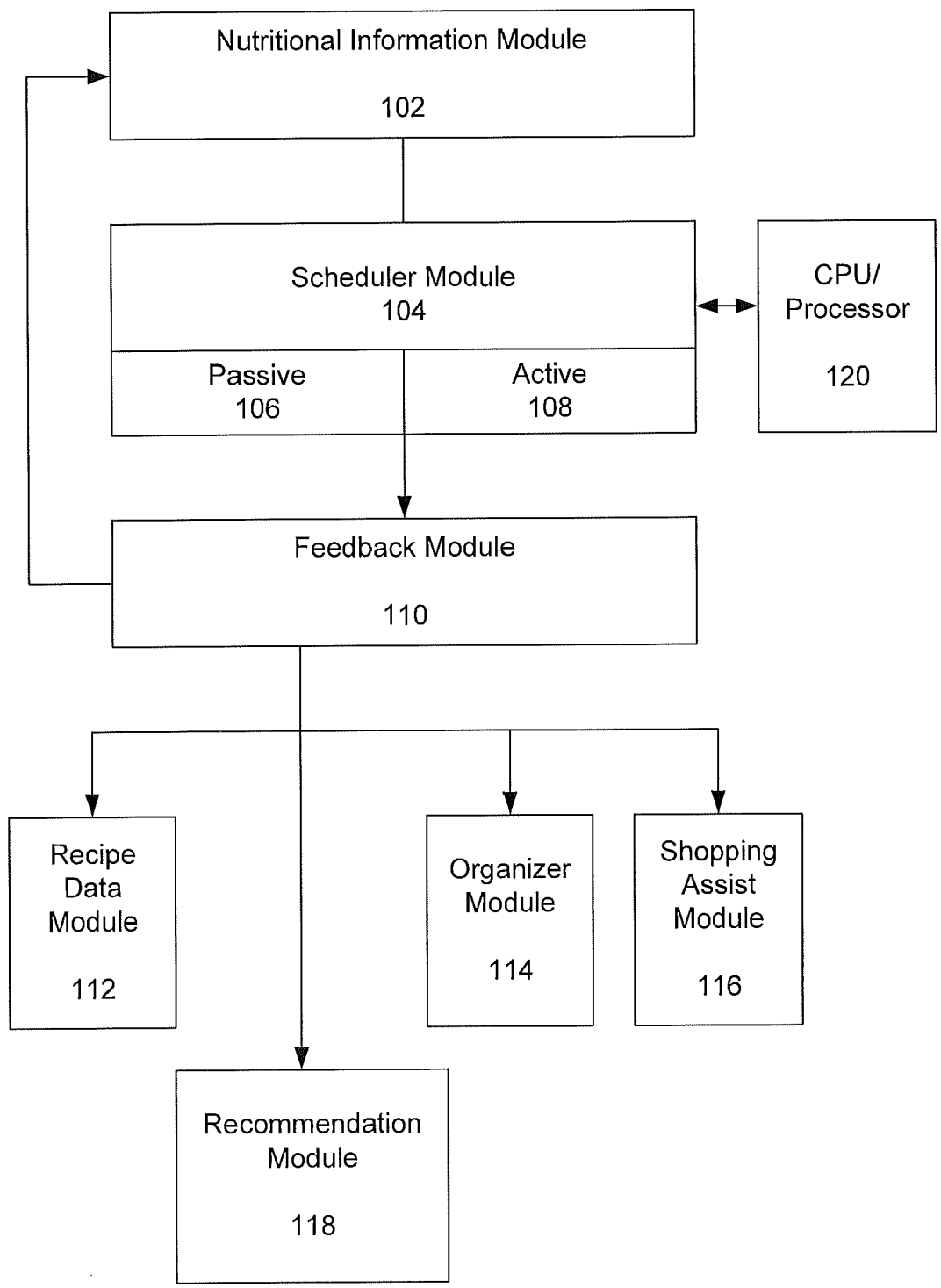
FIG. 1 is a schematic of a system in an exemplary embodiment.

FIG. 1 is a schematic of the system 100 in an exemplary embodiment. In the illustrated embodiment, the system 100 for preparation of food utilizes a nutritional information module 102 which can allow nutritional information to be aggregated for an entire menu along with portion information for any individual recipe. In an exemplary embodiment, the nutritional information module 102 is integrated into a memory storage of a computing device. The memory storage can be volatile such as DRAM, SRAM or other types of memory in development. In some examples, memory storage can also be flash memory or non-volatile such as ROM, PROM, EPROM, EEPROM, or other non-volatile memory. It may be preferable to use volatile memory or perhaps flash so that nutritional information module 102 might be updated as needed. Memory storage of a computing device can also include hard disk storage or any of the various other disk storage, cloud based storage, web based storage, or other types of computer storage, both local and geographically distant.

In one example embodiment the nutritional information module 102 allows for adjustment of portions and caloric values based on ingredients input into the module. Such a nutritional information module 102 may further aggregate the caloric and nutritional information for any particular menu choice. The nutritional information module 102 may allow nutritional information to be aggregated for an entire menu along with portion information and the ability to adjust serving weight by preferred caloric value for any individual recipe. The nutritional information module 102 may also allow for alteration of servings so that the user will not have to adjust the necessary volumes while preparing a meal. In an exemplary embodiment is to provide a system and method for preparation of food whereby the system utilizes a nutritional information module which may allow for alteration of servings so that the user will not have to adjust the necessary volumes while preparing a meal.

The illustrated embodiment includes a scheduler module 104 which may be incorporated and stored in the storage device. An example scheduler module 104 can compile task information for any individual recipe items. Additionally, the schedule module 104 may have any plurality of different task times including a passive task time 106 and/or an active task time 108 and may time stamp the time it takes to prepare any specific recipe. The schedule 104 may compile cook information and store information in a memory bank, e.g., a memory storage of a computing device, for analysis of the individual cook's cooking style and cook time.

In an exemplary embodiment, it is contemplated that a system and method for the preparation of food may be provided whereby the system may schedule and inform the individual user when it is the appropriate time for any one cooking procedure.

The illustrated embodiment also includes a feedback module 110. The feedback module 110 can provide feedback information to the preparer to access their preferences and timing to allow for preferred menus, preparation time, recipes and the like to be provided to the individual user. The feedback module 110 can also use personal time co-efficient to predict the length of time to prepare specific recipe and/or dish. For example, in an exemplary embodiment, the feedback module 110 can allow information to be input into the system by the individual preparer based on the preferences of that individual preparer. The feedback module 110 might allow for predicting the length of time to complete any specific paragraph of a recipe the user has never executed before. The feedback module 110 may also provide for the development of taste profiles depending on the feedback given to the system. In an exemplary embodiment, provides a system and method for preparation of food whereby the system may utilize a schedule module whereby the user may create a menu and add recipes to create multiple course meals showing the critical path by blending and sorting each paragraph element of multiple recipes in the most efficient order.

The illustrated embodiment also includes a recipe data module 112, organizer module 114, shopping assistant module 116 or modules and a recommendation module 118 to help the individual cook decide of menu pairings for any particular recipe as well as source and purchase recipes, required ingredients, and required cookware and utensils.

The recipe data module 112 may be used to store recipe data and can be integrated into a memory storage of a computing device. The organizer module 114 can be integrated into a memory storage of a computing device and may be used to organize menu pairings, purchases, ingredients, etc. The shopping assistant module 116 can be used to generate shopping lists. In yet another exemplary embodiment, it is contemplated to generate a shopping list with ingredients called to the number of servings and serving size. In some embodiments, the system may include an inventory list so that items that are not already owned might not be added to the shopping lists. In some example systems the inventory might keep track of items that have passed the "best before date" such that fresh ingredients might be purchased. The shopping assistant module may also be integrated into a memory storage of a computing device. The recommendation module 118 may track a user or users feedback regarding previous recipes such that the system may make recommendations regarding other recipes. These recipe recommendations might include recommendations regarding main dishes and side dishes. Some may be based on the main ingredient, e.g., chicken, beef, fish, etc.; food origins, e.g., "American food," "Mexican food," "Italian food," etc.; or herbs and spices used in the recipe or a combination of these. For example, a user might have a history of liking chicken and other chicken recipes might be recommended. A user might have a history of liking a specific herb, spice, or some combination of herbs and/or spices. Thus recipes using these herbs and/or spices might be recommended.

One example embodiment may allow for recommendations to be made based on other users who pair the particular menu options. This can be done by the recommendation module which may also combine menu options including different dishes, beverages, desserts and the like. The system may also allow the individual user to mix and match menu options as desired.

The illustrated embodiment also includes a computing device having a microprocessor 120. The computing device can be a personal computer such as a desktop computer or laptop computer. Alternatively, the computing device might be a smart phone, handheld device, or other processor based computing system. Further, the processor might be a microprocessor or other processing circuitry such as digital logic which might be incorporated into a programmable logic device or an application-specific integrated circuit.

Figure 2:
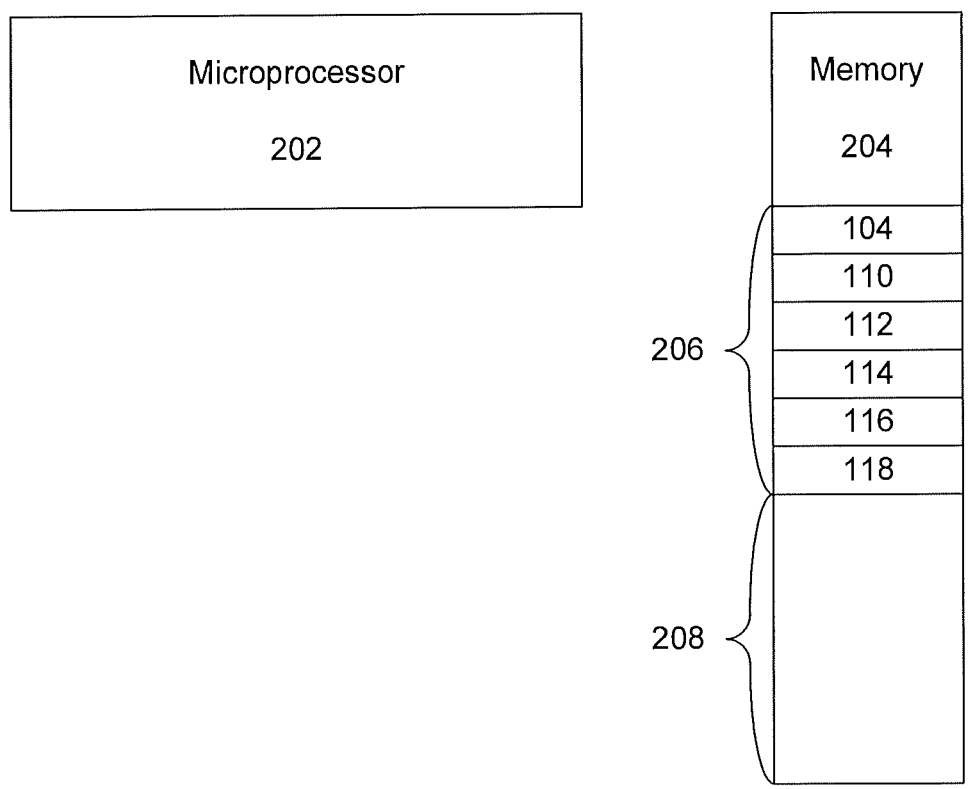
FIG. 2 is a schematic of another system in an exemplary embodiment.

FIG. 2 is a schematic of another system 200 in accordance with an exemplary embodiment. The system 202 may be a computer, hand-held, cellular phone, portable computing device and the like. The system 202 can include a microprocessor 202 that may be any of the various processors described above, for example. The processor 202 in the illustrated embodiment is connected to a memory 204 that includes data portion 206 for storage of data related to the various modules 104, 110, 112, 114, 116, 118. It will be understood that other data might also be stored in memory 204. It will also be understood that, while the figure illustrated as including sequential blocks of memory, the embodiments are not limited to any particular address ranges, orderings, data structures, etc. The memory also includes a code section 208 for storing the instructions that implement the methods described herein. Again, the embodiment is not limited to a particular address range, ordering, data structures, etc. In an exemplary embodiment the code 208 may comprise of proprietary software stored in memory 204 of a device.

Applicants also note that the systems described herein might be designed using different functional blocks. For example, some processors might also include memory on the same die as the processing circuitry to form a "system on a chip." Other configurations of various computer systems, currently known or later developed, may also be used in conjunction with the systems and methods described herein.

In an exemplary embodiment the system may allow for download and viewing of appropriate task functions as desired by the individual user.

Figure 3:
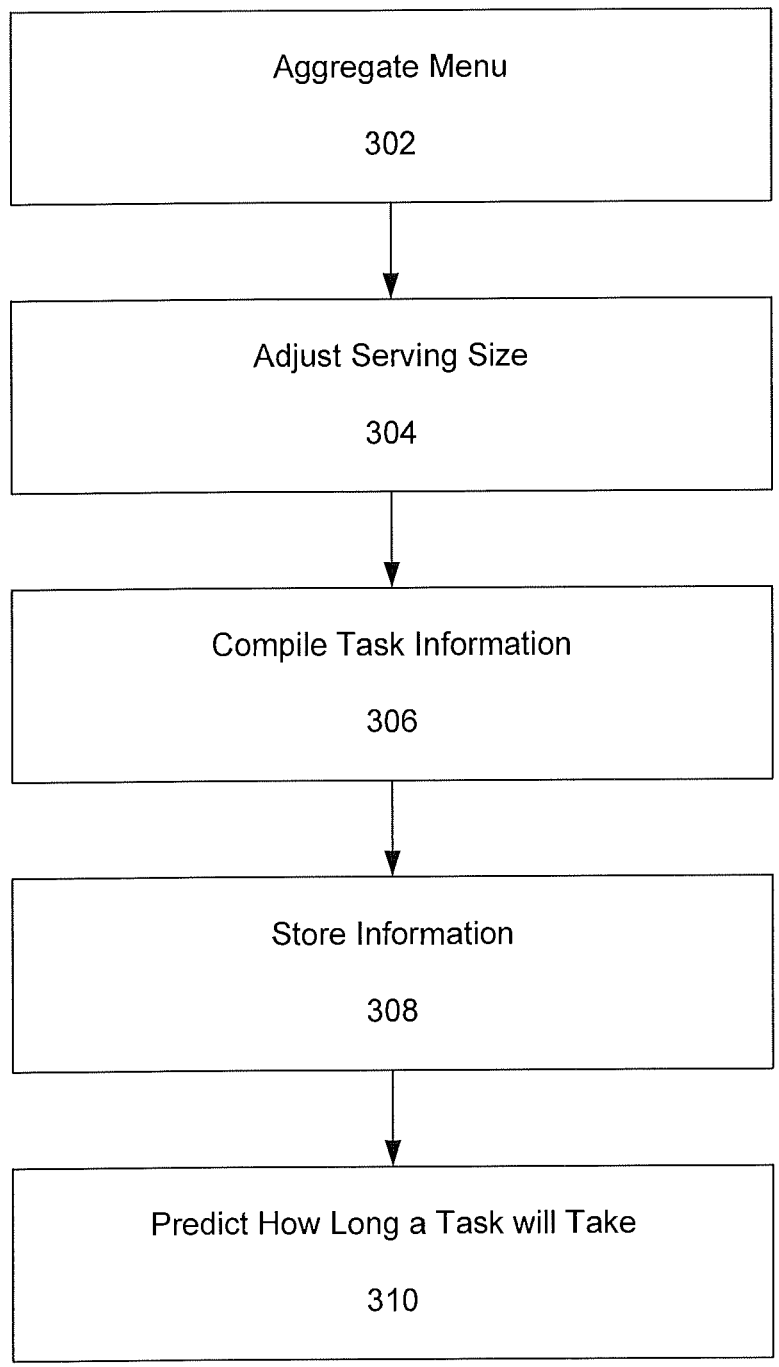
FIG. 3 is a flowchart illustrating an example method of an exemplary embodiment.

FIG. 3 is a flowchart illustrating an example method 300 of an exemplary embodiment. In step 302 nutritional information is aggregated for an entire menu along with portion information. For example, a system may utilize a nutritional information module which allows nutritional information to be aggregated for an entire menu along with portion information.

Nutritional information may come from a variety of sources. The recipe itself may include nutritional information. Further, a database of nutritional information on individual ingredient may be accessed. This database can be on a computer used to implement the system, stored on an external hard drive, accessed over the internet, etc. The data for such a database might be generated using a variety of sources such as the internet, grocery stores, food providers, etc. This information can then be aggregated for the entire menu.

In step 304 serving weight is adjusted by preferred caloric value for an individual recipe. For example, the portion size, e.g., weight may be modified based on, for example, desired calories such that, if a particular recipe portion has 200 calories and an individual only wishes to consume 100 calories then the portion size can be cut in half. While the example measured portions by weight, it will be understood that portions may be measured by weight, volume, or other common measures of portion size, including a combination of weight for some menu items and volume for other menu items, e.g., in the same planned meal.

In step 306 task information is compiled for individual recipe items cook information. For example, a system may also utilize a scheduler module which compiles task information for any individual recipe items per paragraph. The schedule module can have any plurality of different task times including a passive task time and/or an active task time and may time stamp the time it takes to prepare any specific recipe. The scheduler can also compile cook information and store information in a memory bank for analysis of the individual cook's cooking style and cook time.

In step 308 information is stored in a memory bank for analysis of an individual cook's cooking style and cook time. The information stored may be the information that was compiled by the scheduler. The memory may be one or more of the various forms of writable memory or data storage.

In step 310 a personal time coefficients is used to predict how long it should take for any particular menu choice preparation. For example, a system may also provide a feedback module which uses personal time coefficients to predict how long it should take for any particular menu choice preparation. Although the method has been described with respect to various functional blocks, it will be understood that the method may also be implemented without using the functional blocks described herein. For example, the functionality of the modules may be changed, shared, redistributed between different modules, or otherwise broken into different functional elements to perform the steps of the methods described herein.

Some embodiments of the method provide a recipe data module, organizer module, shopping assistant modules and a recommendation module to help the individual cook decide of menu pairings for any particular recipe as well as source and purchase recipes, required ingredients, and required cookware and utensils. These modules may provide various functionality. The recipe data module can include data associated to various recipes. These recipes might come from cookbooks, the internet, individual users, chefs, food companies, or various other sources of recipe information. In an exemplary embodiment of the present invention is to provide a system and method for preparation of food whereby the system allows the individual user to browse and purchase individual recipes from a remote server location. The data can be stored in the recipe data module. The organizer module may be used to organize various aspects of the menu and the shopping assistant modules can be used to generate shopping lists. The recommendation module can make recommendations, for example, based on individual user feedback, feedback from a large variety of users, or data from other sources. Again, it will be understood that although the method has been described with respect to various functional blocks, it will be understood that the method may also be implemented without using the functional blocks described herein.

Some embodiments of the method further comprise time stamping the time it takes to prepare any specific recipe. This data might be used to estimate time to complete other recipes and may be preparer specific. For example, some cooks may be faster than others. Accordingly, the system may use data specific to a particular cook or combination of cooks with similar cooking times on the same or similar items when calculating a time estimate.

Some embodiments of the method provide for compiling task information for any individual recipe items base on step of each paragraph of the recipe. In some cases these tasks may be broken into smaller sub-steps rather than kept as individual paragraph base steps.

Additionally, in an exemplary embodiment, a system and method for preparation of food is provided whereby the system may have a task window feature whereby the task window is bounded by the earliest time as task can be started, and produce an acceptable serving, and the start of the next dependent task. More flexible tasks can be rescheduled to earlier point in time. As servings scale the active time grows. If it overflows the task window a bottleneck is flagged. All or a portion of any task can be reassigned to anther chef.

The systems and methods described herein may allow for more efficient use of a food preparers time. An example system and method includes a nutritional information module, and a scheduler module. The system and method for preparation of food whereby the system allows for delicious and healthy meals that can be easy to prepare and guide the preparer through the cooking process. An example system allows the individual user to select and pair recipes and beverages when planning menus and meal plans. Other examples may provide suggestions to the user.

In yet another exemplary embodiment, a system and method for the preparation of food is provided whereby the system may allow the individual preparer to find and purchases the required ingredients, cookware, utensils and other tools required to prepare the desired food. This may be done by preparing a shopping list that might be taken to one or more stores to make purchase. In another embodiment, the purchases might be made by the system, e.g., over the internet or other communications system or network. The purchase might be made for local pickup, local delivery, or might be delivered over a distance using, e.g., a postal or package delivery service. For example, cookware, utensils and other tools might be shipped using the United States Postal Service. It will be understood that ingredients may generally be delivered from local providers, but that the systems and methods described herein are not limited in this way. It is not uncommon for foods, spices, or other ingredients to be shipped great distances.

For example, the system may allow for use of the user's location to find venders of all the required ingredients in the shopping list. With this information, the system may find and provide a default list of multiple ingredient vendors searching for each item in the vender's inventory in descending preferred order. In yet another exemplary embodiment, assign any vender as the default vender for any specific ingredient.

In another exemplary embodiment, a system and method is provided for the preparation of food whereby the system allows for the development of taste profiles depending on the feedback given to the system. The taste profile may be for a particular user, a particular family, or a wide range of users. For example, when a wide range of users like a particular item, this may be taken into account for future recommendations. Additionally, information for users who appear to have generally similar likes and dislikes might be used to develop a taste profile for a user.

Yet another exemplary embodiment of the present invention may be a system and method for the preparation of a food dish whereby the system allows for configuration of the system depending on individual user needs.

What is claimed is:

1. A food preparation optimization system, comprising:
   a computing device comprising a microprocessor and a memory,
   the memory capable of storing:
   a nutritional information module;
   a scheduler module configured to compile task information for a plurality of entire menus, each entire menu of the plurality of entire menus comprising a recipe that lists a recipe item and paragraph element,
   the paragraph element comprising step, the step comprising sub-step, the recipe item having a passive task time and an active task time,
   the scheduler module configured to enable the computing device to optimally blend and sort the paragraph element of the recipe of the entire menu, the scheduler module configured to time stamp the time it takes to prepare the recipe;
   a recommendation module for recommending a menu pairing, wherein the menu pairing comprises a side dish and further wherein the recommendation module is configured to track feedback regarding previous recipes so as to make recommendations, the feedback comprising one of individual user feedback and feedback from a plurality of users; and
   a feedback module configured to predict a length of time for completing each step of the recipe of the each entire menu and to determine a cook's coefficient for predicting a duration for preparing each recipe of the each entire menu, the feedback module configured to enable the computing device to facilitate alteration of a serving, whereby adjusting an ingredient quantity while preparing the recipe of the each entire menu is eliminated; wherein the feedback module is configured to develop one or more taste profiles based on the feedback; and
   wherein an individual user's location may be determined so as to locate vendors of any of required ingredients of the recipe.

2. The system of claim 1, wherein the nutritional information module is configured to facilitate adjusting portion and caloric value based on entered data relating to ingredient.

3. The system of claim 1, wherein the nutritional information module is configured to aggregate caloric information and nutritional information for each entire menu.

4. The system of claim 1, wherein the scheduler module is configured to provide information regarding an amount of time for performing the sub-step of the step of the recipe.

5. The system of claim 1, wherein the scheduler module comprises a passive task time module configured to provide information regarding an amount of additional time for performing the sub-step of the step of the recipe.

6. The system of claim 1, wherein the feedback module is configured to determine a personal time coefficient for predicting a length of time required for performing the sub-step of the step of the recipe hitherto unperformed.

7. The system of claim 1, further comprising:
   of a recipe data module, an organizer module, and a shopping assistant module.

8. The system of claim 1, further comprising: wherein the recommendation module further recommends for recommending of a menu pairing, a beverage pairing, and a dessert pairing for the recipe of the each entire menu.

9. The system of claim 1, further comprising:
   of a recipe data module, an organizer module, and a shopping assistant module; and
   a recommendation module for recommending of a menu pairing, a beverage pairing, and a dessert pairing for the recipe,
   wherein the nutritional information module is configured to facilitate adjusting portion and caloric value based entered data relating to ingredient,
   wherein the nutritional information module is configured to aggregate caloric information and nutritional information for the each entire menu,
   wherein the scheduler module is configured to provide information regarding an amount of time for performing the sub-step of the step of the recipe,
   wherein the scheduler module comprises a passive task time module configured to provide information regarding an amount of additional time for performing the sub-step of the step of the recipe, and
   wherein the feedback module is configured to determine a personal time coefficient for predicting a length of time required for performing the sub-step of the step of the recipe hitherto unperformed.

10. A food preparation optimization system, comprising:
    a processor; and
    a memory capable of storing a set of instructions for enabling the processor to:
    aggregate nutritional information for a plurality of entire menus along with portion information, each entire menu comprising a recipe, each recipe listing a recipe item and a paragraph element, the paragraph element comprising a step, the step comprising a sub-step;
    optimally blend and sort the paragraph element of the recipe of the each menu;
    facilitate alteration of a serving, whereby adjusting an ingredient quantity while preparing the recipe of the each entire menu is eliminated;
    adjust a serving quantity by applying a preferred caloric value to the recipe;
    compile task information for the recipe item and a cook's information for determining a task time corresponding to the sub-step of the step of the recipe of the each entire menu and for facilitating time-stamping a predicted duration for preparing the recipe of the each entire menu;
    recommend a menu pairing using a recommendation module, wherein the menu pairing comprises a side dish and further wherein the recommendation module is configured to track feedback regarding previous recipes so as to make recommendations;
    time stamp the time it takes to prepare the recipe;
    store the task information and the cook's information in the memory for analyzing cooking style and cooking time; and
    determine cook's coefficient for predicting a duration for preparing a recipe of the each entire menu.

11. The system of claim 10, wherein the memory is configured to store an instruction for causing the processor to adjust a portion and a caloric value based on the preferred caloric value in relation to the recipe listing the recipe item.

12. The system of claim 10, wherein the memory is configured to store an instruction for causing the processor to aggregate caloric information and the nutritional information in relation to the recipe.

13. The system of claim 10, wherein the memory is configured to store an instruction for causing the processor to provide information regarding an amount of time for performing the sub-step of the step of the recipe.

14. The system of claim 10, wherein the memory is configured to store an instruction for causing the processor to provide information regarding an amount of additional time for performing the sub-step of the step of the recipe.

15. The system of claim 10, wherein the memory is configured to store an instruction for causing the processor to determine personal time coefficient for predicting a length of time required for performing the sub-step of the step of the recipe hitherto unperformed.

16. The system of claim 10, further comprising:
of a recipe data module, an organizer module, and a shopping assistant module.

17. The system of claim 10, wherein the memory is configured to store an instruction for causing the processor to recommend of a menu pairing, a beverage pairing, and a dessert pairing for the recipe of the each entire menu.

18. The system of claim 10, further comprising:
of a recipe data module, an organizer module, and a shopping assistant module,
wherein the memory is configured to store an instruction for causing the processor to adjust portion and caloric value based on the preferred caloric value in relation to the recipe listing the recipe item,
wherein the memory is configured to store an instruction for causing the processor to aggregate caloric information and the nutritional information in relation to the recipe,
wherein the memory is configured to store an instruction for causing the processor to provide information regarding an amount of time for performing the sub-step of the step of the recipe,
wherein the memory is configured to store an instruction for causing the processor to provide information regarding an amount of additional time for performing the sub-step of the step of the recipe,
wherein the memory is configured to store an instruction for causing the processor to determine personal time coefficient for predicting a length of time required for performing the sub-step of the step of the hitherto unperformed, and
wherein the memory is configured to store an instruction for causing the processor to recommend of a menu pairing, a beverage pairing, and a dessert pairing for the recipe.

19. A method of optimally preparing food, comprising:
aggregating nutritional information for each entire menu of a plurality of entire menus along with portion information by way of a memory capable of storing a set of instructions for enabling a processor, the each entire menu comprising a recipe, the recipe listing a recipe item and a paragraph element, the paragraph element comprising a step, the step comprising a sub-step;
optimally blending and sorting the paragraph element of the recipe of the each entire menu by way of a memory capable of storing a set of instructions for enabling a processor;
facilitating alteration of a serving, thereby eliminating adjusting an ingredient quantity while preparing the least one recipe of the each entire menu;
adjusting a serving quantity by applying a preferred caloric value to the recipe;
compiling task information for the recipe item and a cook's information for determining a task time corresponding to the sub-step of the step of the recipe of the each entire menu and for facilitating time-stamping a predicted duration for preparing the recipe of the each entire menu;
recommending a menu pairing using a recommendation module, wherein the menu pairing comprises a side dish and further wherein the recommendation module is configured to track feedback regarding previous recipes so as to make recommendations;
time stamping the time it takes to prepare the recipe;
storing the task information and the cook's information in the memory for analyzing cooking style and cooking time; and
determining cook's coefficient for predicting a duration for preparing each recipe of the each entire menu by the processor; and
wherein an individual user's location may be determined so as to locate vendors of any of required ingredients of the recipe.

20. The method of claim 19, further comprising:
providing a recipe data module, an organizer module, a shopping assistant module, and wherein the recommendation module for facilitating of a menu pairing, facilitates of sourcing and purchasing ingredient, and sourcing and purchasing required cookware and utensils.

21. The method of claim 19, further comprising:
providing information regarding an amount of time for performing the sub-step of the step of the recipe.

22. The method of claim 19, wherein the compiling step comprises compiling task information relating to the sub-step of the step of the recipe.

23. The method of claim 19, further comprising:
providing of a recipe data module, an organizer module, a shopping assistant module, and a recommendation module for facilitating of pairing a menu, sourcing and purchasing ingredient, and sourcing and purchasing required cookware and utensils; and
providing information regarding an amount of time for performing the sub-step of the step of the recipe of the each entire menu, and
wherein the compiling step comprises compiling task information relating to the sub-step of the step of the recipe of the each entire menu.

* * * * *